United States Patent [19]

Ryan

[11] Plant 4,449

[45] Aug. 14, 1979

[54] IMPATIENS PLANT

[76] Inventor: John J. Ryan, 39877 Sundale Dr., Fremont, Calif. 94538

[21] Appl. No.: 875,600

[22] Filed: Feb. 6, 1978

[51] Int. Cl.[2] ..... A01H 5/00
[52] U.S. Cl. ..... Plt./68
[58] Field of Search ..... Plt./68

[56] References Cited

U.S. PATENT DOCUMENTS

P.P. 2,206 12/1962 Rubel ..... Plt./60

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Cheyenne, and discovered by me in commercial greenhouses in Fremont, Calif. Cheyenne isn't close to any of the varieties presently on the market. Cheyenne is particularly characterized by dark green foliage with a tint of red (adding to the darkness of the foliage); very floriferous; a medium bright red flower with a distinctive light eye; different color breaks (as many as 6) on the flowers with the three most common ones being rose-red, flecked red on white and orange; and an upright growth habit with moderate stem size.

1 Drawing Figure

BACKGROUND OF THE INVENTION

The present new variety (seedling) was discovered by me in a commercial greenhouse in Fremont, Calif., as a result of the cross pollination of unpatented pistil parent 75-24 and the unpatented pollen parent 75-7.

Asexual reproduction of my new cultivar by terminal or stem cuttings grown in pots in a plastic (polyethylene) greenhouse in Fremont, Calif., under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Cheyenne is not that close to any of the varieties presently on the market. Part of the problem is a lack of good reds on the market. Red Magic has some similar characteristics.

1. Cheyenne is more floriferous than Red Magic.
2. Foliage is dark green with a red tint.
3. Flower is brighter than that of Red Magic.
4. Cheyenne commonly shows color breaks where as Red Magic does not. Cheyenne shows as many as six different color breaks; (1) rose-red (51B RHS), (2) pink (51A RHS), (3) pinked-white (36D RHS), (4) flecked red on white, (5) red-purple (73A RHS), and (6) orange (33A RHS) but the three most common occurring color breaks are the rose-red (51B), flecked red on white, and orange (33A). These three most common, color breaks occur on approximately 2% of the blossoms.

DESCRIPTION OF THE PHOTOGRAPH

The accompanying colored photograph of the entire plant illustrates the overall appearance of the cultivar Cheyenne with a slightly darker color (especially shown by loss of brightness in flower color). Under high light, the red tint in the foliage increases and the brightness of the flower decreases.

Supplemental photographs B, C and D show the six color breaks possible. Photo B is a close up of the same blossom in photo C. This blossom shows five of the color breaks that appear: (1) rose-red (51B RHS), (2) pink (51A RHS), (3) pinked-white (36D RHS), (4) flecked red on white and (5) a red-purple (73A RHS).

Photo D is submitted to show the sixth color break; the orange one (33A RHS).

Photo D shows six (6) blossoms. The three orange blossoms are Shoshoni blossoms (U.S. Pat. application, Ser. No. 875,597 filed Feb. 6, 1978) and the other three blossoms are typical blossoms of Cheyenne. The orange color break is clearly seen on the Cheyenne blossom being identified by the pointer.

DETAILED DESCRIPTION

The following detailed description of Cheyenne was based on observations made of the new cultivar on Jan. 15, 1977.

I. PLANT

Name: Cheyenne.
Origin: Seedling of cross pollination of unpatented pistil parent 75-24 and unpatented pollen parent 75-7.
Form: Upright.
Height to flowering: 30 cm.
Growth: Moderate.
Type of cutting: Terminal or stem.
Root time: Typical, 10–14 days.
Rooting habit: Fast, dendritic.

II. FOLIAGE

Arrangement: Lower leaves of any break opposite (usually just one set); upper foliage of any break is whorls of 3 to 5 (mostly 5's).
Shape: Older leaves of any break oblanceolate, newer leaves are elliptic.
Tip: Broadly acuminate.
Base: Attenuate.
Margin: Ciliate at base, serrulate on distal end.
Veination: Pinnate.
Size: Blade and petiole 10.0 cm. to 16.0 cm., length of blade 7.5 cm. to 13.0 cm., width of blade at widest point 3.0 cm. to 4.5 cm.
Surface: Glabrous.
Variegation: None.

Color:

1. *Petiole.*—a. Upper 48 C. b. Lower 47 B.
2. *Veins.*—a. Upper 145 C. b. Lower 48 C.
3. *Leaf.*—a. Upper 137 A. b. Lower 138 C.

III. STEM

Color: 148 A

Internode:

1. *Length.*—Moderate.
2. *Size.*—Moderate.

Node expanded (relative to internode): Slightly expanded.

Breaking action: Moderate to good.

IV. FLOWER

Form: Typical.

Borne: End of branches, terminal.

Blooming habit:

1. *Relative number.*—Profuse.
2. *Time to flowering.*—Average.
3. *Longevity.*—Typical, 3 to 5 days.

Size of mature flower: First flower on a plant may be small.

1. *Length.*—5.0 cm. to 5.5 cm.
2. *Width.*—5.0 cm. to 5.5 cm.
3. *Spur.*—5.5 cm. to 6.5 cm.

Color: Lighter red under high light and heat.

| | |
|---|---|
| 1. *Eye*: From white 56 D to red-purple 66A. | |
| 2. *Middle* | 46 B. |
| 3. *Edge* | |

-continued

| | |
|---|---|
| 4. *Pedicel*: 194 C. | |

V. REPRODUCTIVE ORGANS

Stamen:

| | |
|---|---|
| 1. *Anthers*: | Typical, fused hood over pistil. |
| 2. *Filaments*: | |
| 3. *Pollen.* a. Color: 158 C. b. Abundance: Typical, plenty. | |

Pistils:

| | |
|---|---|
| 1. *Style* | Typical. |
| 2. *Ovaries* | |

VI. OTHER CHARACTERISTICS

One of the best cutting producers, considering how floriferous it is.

I claim:

1. A new and distinct form of Impatiens plant as described and illustrated, known by the cultivar name Cheyenne, and particularly characterized by dark green foliage with a tint of red; many flowers; a medium bright red flower with a distinctive light eye; three different commonly occurring color breaks on the flowers; and an upright growth habit with moderate stem size.

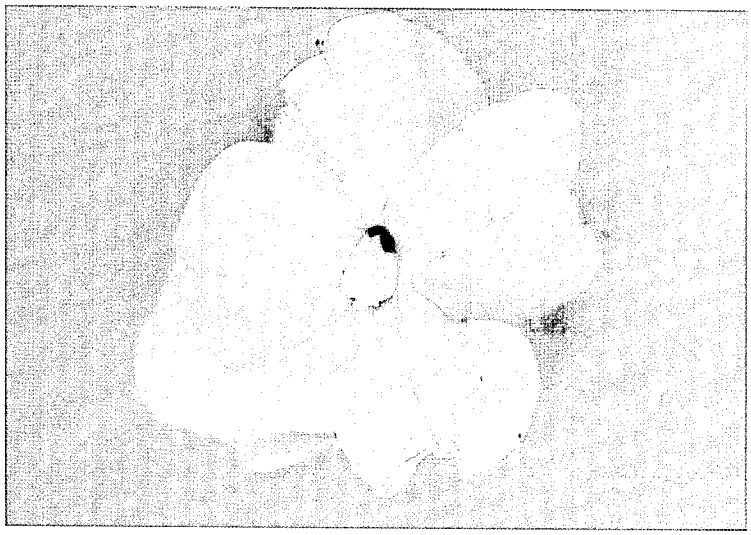
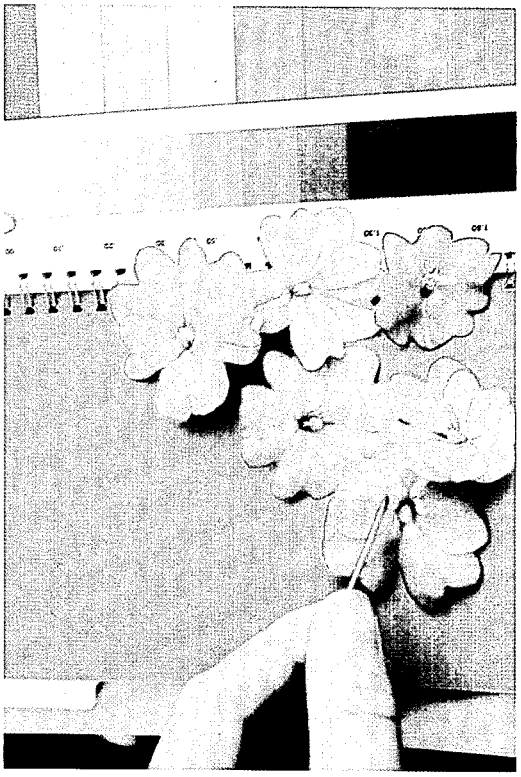
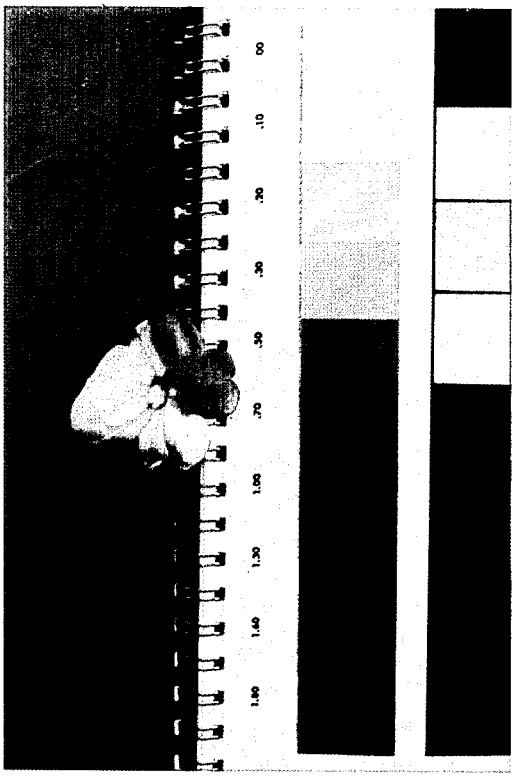

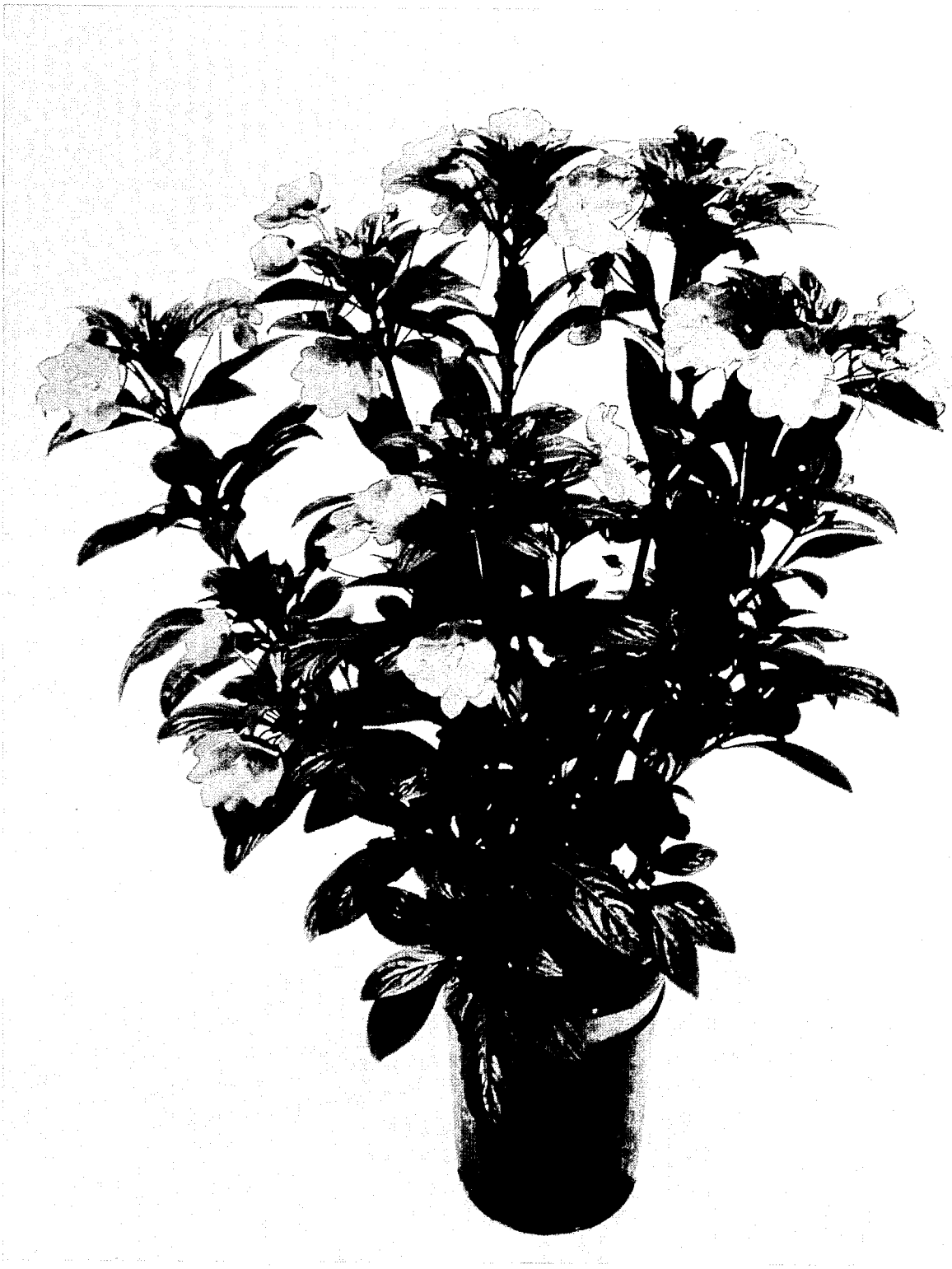

* * * * *